United States Patent
Simon

(10) Patent No.: US 7,190,795 B2
(45) Date of Patent: Mar. 13, 2007

(54) HEARING ADJUSTMENT APPLIANCE FOR ELECTRONIC AUDIO EQUIPMENT

(76) Inventor: Henry Simon, 3211 East Ave., Rochester, NY (US) 14618

( * ) Notice: Subject to any disclaimer, the term of this patent is extended or adjusted under 35 U.S.C. 154(b) by 101 days.

(21) Appl. No.: 10/681,718

(22) Filed: Oct. 8, 2003

(65) Prior Publication Data

US 2005/0078838 A1 Apr. 14, 2005

(51) Int. Cl.
*H04R 29/00* (2006.01)
*A61H 5/00* (2006.01)

(52) U.S. Cl. ......................... 381/60; 600/559
(58) Field of Classification Search .................. 381/60; 600/558–559; 73/585
See application file for complete search history.

(56) References Cited

U.S. PATENT DOCUMENTS

| | | | |
|---|---|---|---|
| 3,986,049 A | 10/1976 | Campbell et al. | |
| 4,233,665 A | 11/1980 | Maehashi et al. | |
| 5,130,665 A | 7/1992 | Walden | |
| 5,138,665 A | 8/1992 | Ito | |
| 5,197,332 A | 3/1993 | Shennib | |
| 5,233,665 A | 8/1993 | Vaughn et al. | |
| 5,434,923 A | 7/1995 | Honda | |
| 5,500,902 A | 3/1996 | Stockham, Jr. et al. | |
| 5,781,848 A | 7/1998 | Komoda | |
| 6,028,944 A | 2/2000 | Markow et al. | |
| 6,104,822 A | 8/2000 | Melanson et al. | |
| 6,322,521 B1 | 11/2001 | Hou | |
| 6,442,278 B1 | 8/2002 | Vaudrey et al. | |
| 6,574,342 B1 * | 6/2003 | Davis et al. | 381/314 |
| 2002/0126859 A1 | 9/2002 | Ullrich | |
| 2002/0172376 A1 | 11/2002 | Bizjak | |
| 2002/0183648 A1 | 12/2002 | Hou | |
| 2003/0002683 A1 | 1/2003 | Vaudrey et al. | |
| 2003/0064746 A1 * | 4/2003 | Rader et al. | 455/550 |

OTHER PUBLICATIONS

Edgar Villchur, "Signal Processing to Improve Speech Intelligibility in Perceptive Deafness", The Journal of the Acoustical Society of America, vol. 53, No. 6, 1973, pp. 1646-1657.
David Pedro Pasco, Ph.D., "Frequency Responses of Hearing Aids", doctored dissertation, Central Institute for the Deaf(1974), pp. 12-14, Fig. 2.
Lippmann, R. P., "Study of multichannel amplitude compression and linear amplification for persons with sensorineural hearing loss", J. Acoustical Society America, Feb. 1981, pp. 524 through 534, Copyright 1981 Acoustical Society of America.

* cited by examiner

*Primary Examiner*—Xu Mei
(74) *Attorney, Agent, or Firm*—Thomas R. FitzGerald, Esq.; Hiscock & Barclay, LLP

(57) ABSTRACT

An electronic device with audio output, such as a television, is adjusted to the customized listening profile of a user with a user interface module 100 and a control module 110. A user sets the level of amplification for the center or test frequency of a number of audio frequency bands. The control module generates tones at the test frequencies and the user adjusts the amplification of each tone until the user is satisfied with hearing that tone. The other frequencies in the band are adjusted by the same amount as the test tone.

34 Claims, 4 Drawing Sheets

HEARING ADJUSTMENT APPLIANCE FOR ELECTRONIC AUDIO EQUIPMENT

BACKGROUND

Hearing loss is the most prevalent chronic health condition in the United States with one out of ten Americans suffering some level of loss. Despite the fact that the loss can be mitigated through the use of hearing aids only 25% of affected Americans make use of them. The reasons for this are varied but include cost, physical discomfort, lack of effectiveness in some specific listening situations, societal perception, and unawareness of the hearing loss.

Traditionally hearing loss is diagnosed by a medical specialist using an audiometer. This tool measures the hearing loss parameters of an individual in comparison to a set of reference parameters to develop a hearing loss profile. This profile is then used as the basis for customizing a hearing aid for the individual. These tests are typically performed in a noise-free environment where impediments to hearing are not present.

Calibration of the testing system is required for any results to be useful in mitigating for hearing loss. Mainly, this means that the acoustical pressure delivered to the individual's ear drum must be known for the various settings on the testing machine. Unfortunately this pressure varies from individual to individual even using the same equipment. To correct for this a coupler is typically used where the delivered pressure is known on an absolute basis.

Testing of the individual's hearing loss is performed by producing a pure tone that is delivered to the subject, in a controlled manner as described above, through an earphone in a headset. The individual responds by signaling when he hears the tone. The test operator will increase or decrease the amplification as required for each frequency. The process is repeated until a set number of reversal points have been reached. The individual's hearing threshold is defined as the amplification level where an individual hears the tone 50% of the time. In order to determine the hearing loss profile the hearing threshold of the individual is typically tested at seven different frequencies (125, 250, 500, 1000, 2000, 4000, and 8000 Hz). If the hearing threshold between any two adjacent frequencies (500 to 8000 Hz) exceeds a critical value (typically 20 dB) then a test at an intermediate frequency is performed. This can result in a maximum of eleven frequencies being tested (125, 250, 500, 750, 1000, 1500, 2000, 3000, 4000, 6000, and 8000 Hz).

While developing the hearing loss profile in this way permits hearing aid customization that works well in noise free environments, performance may decrease dramatically in the presence of noise. This is a serious limitation as an individual is likely exposed to many environments in which acoustic noise is prevalent, such as a moving automobile or crowded location.

Conventional hearing tests conducted by audiologists establish a general standard of 0–20 decibels over a range of 250 to 8000 Hz as a manual hearing range. Some studies show that within the general hearing range normal-hearing people have a distinct profile and are more sensitive to higher sounds than to lower sounds. See David Pedro Pascoe, Ph. D., "Frequency Responses of Hearing Aids", doctored dissertation, Central Institute for the Deaf, (1974), pages 12–14, FIG. 2. Those studies suggest that a flat threshold hearing aid profile could be modified to reduce the threshold amplification of low frequencies and/or increase the threshold amplification of high frequencies and thereby generate a fine tuned hearing profile that closely resembles normal-hearing people. The studies indicate that perceived speech is more intelligible when the threshold is fine tuned to the normal hearing profile. In other words, small adjustments are made to alter the threshold from a flat profile in the 0–20 dB range to a frequency dependent profile.

A second problem with the traditional form of testing is its reliance on a specialist to perform the test. This problem is three-fold. First, an individual must make the commitment, in the face of societal pressure, to admit that they have a medical problem. Second, the entire process can be expensive and is not typically paid for by insurance. Third, these specialists are not always readily available to an individual making the process inconvenient and time consuming.

A recent alternate approach to generating an individual's hearing loss profile, independent of an audiometer or specialized operator, is disclosed by Hou in US2002/0183648A1. Also disclosed is the idea of modifying a personal audio system with an individual's hearing loss profile to compensate for that particular loss.

The testing method discussed by Hou involves three basic steps. The first is to test a reference individual, someone who does not suffer from hearing loss, to generate a set of baseline parameters for a specific audio system. In other words, to calibrate the audio system to a reference individual's hearing adjustment profile. Like the traditional hearing test, this method plays pure tones at the same series of frequencies using turning points to determine the hearing threshold. The second step tests the subject individual to determine their hearing parameters in response to the same audio system. The two sets of values are then compared to generate the hearing loss profile. This profile can then be use for various purposes, including for compensation of a personal audio system for the subject individuals hearing loss. Hou's method also allows for manual manipulation of the hearing loss profile to account for possible discrepancies in the testing process.

Hou's approach has a number of limitations. First, because the process is used to generate a hearing loss profile, the audio system used for the testing must still be calibrated, in this case, to the hearing profile of the reference individual. If the system were not calibrated then the results could not accomplish the stated purposes. Second, if the reference and subject individual's physical positions or orientations with respect to the audio source were not identical, comparisons of the testing data could result in an inaccurate hearing loss profile and a correspondingly ineffective compensation of the audio system. Finally, if the background noise varies between the reference and subject individual's tests, the resulting hearing loss profile could be similarly inaccurate, resulting in inappropriate audio system compensation.

SUMMARY

The invention provides a method that eliminates the need to calibrate the acoustic pressure delivered by any audio system to the eardrum, or to reference a particular individual's hearing loss profile to another profile, while allowing a listener to customize any audio system in accordance with the listener's hearing profile. This method can be used to modify existing audio systems or create new ones that are capable of measuring and compensating for an individual's hearing profile.

This is accomplished by a self-administered hearing test, performed in an uncontrolled audio environment, preferably the typical listening environment for the audio system being compensated. It uses an electronic tone generator that provides a constant signal level, independent of test frequency, to the input of an electrical audio amplifying circuit. It allows the user to step through each frequency band and it generates a tone representative of each band. In particular, the tone may be the center frequency of each band. The tone may be played at a number of different levels of amplification. The user sets a minimum threshold level and may optionally set a maximum level. The level for each representative frequency is individually set. The settings are saved in a memory and are applied to the audio apparatus during normal operation to adjust the sound level in each frequency band in accordance with the representative tone setting previously established.

The invention thus records a self-test hearing adjustment profile of a listener. The hearing adjustment profile is a set of frequency bands and corresponding amplification levels for each band that a user selects by self-testing their hearing with one or more representative frequencies in each band. The hearing adjustment profile is different from the hearing loss profile that is measured by an audiologist. The uncontrolled audio environment may be any environment where the user is not acoustically isolated from ambient noise. In other words, it is any place other than inside a sound controlled booth used by audiologists to test patients.

This results in the audio transfer characteristics of the audio system and the specific listening environment becoming part of the self-assessed hearing profile. While absolute hearing loss is not measured, the ability to modify an audio system in a typical listening environment to an individual's hearing profile is greatly improved and the process to determine it is greatly simplified.

The generated profile can be stored with multiple other profiles in provided memory. This means that multiple individuals could use the device or multiple listening environments could be stored. Also, as the process for changing the hearing parameters is quick and easy, the user can retest and readjust the compensation at any time.

In general the invention is a device that can be used with any electronic audio system. The device has two modes, a test/setup mode, and an operating mode.

BRIEF DESCRIPTIONS OF THE DRAWINGS

DETAILED DESCRIPTION

Figure 1:
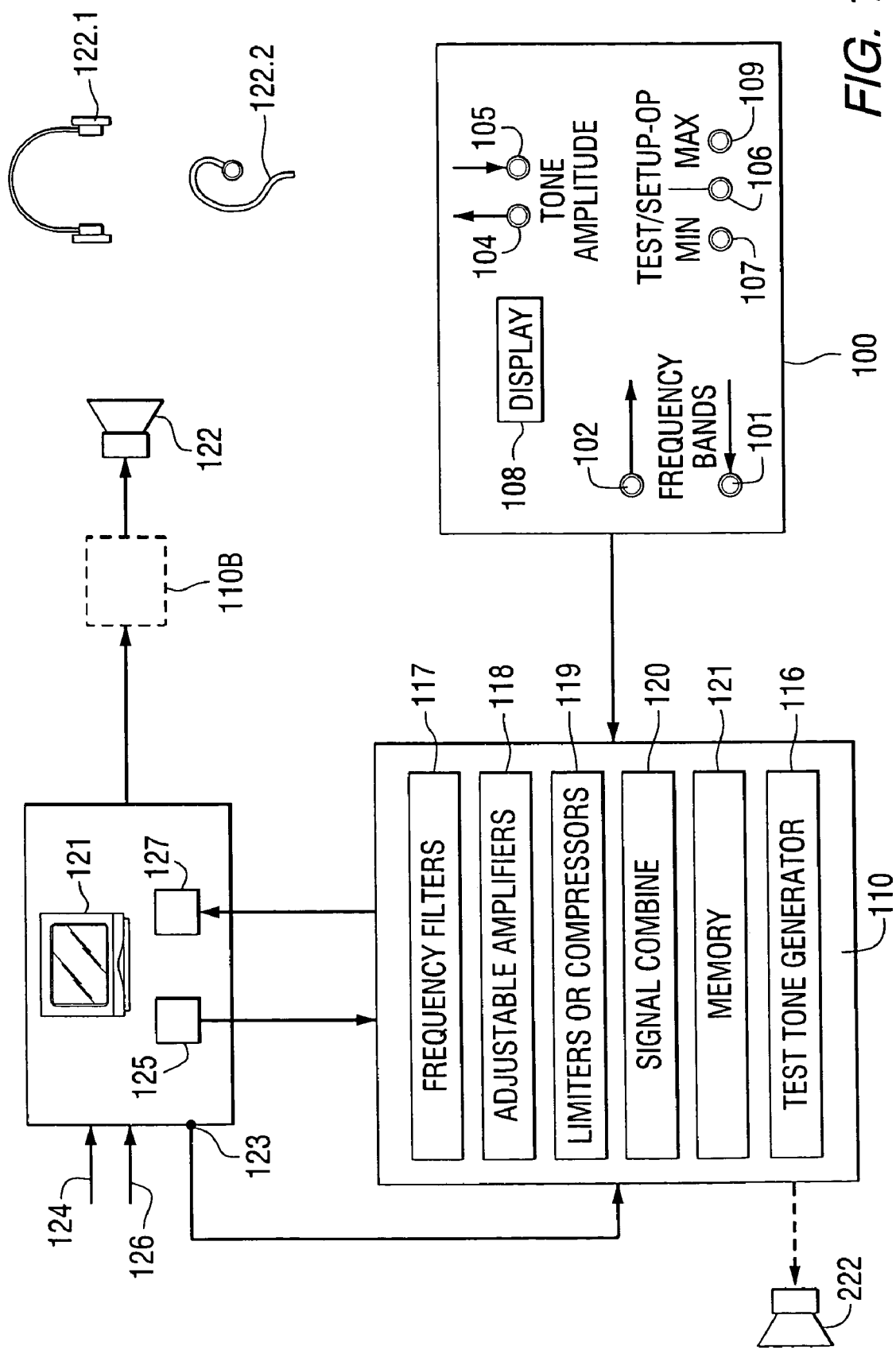
FIG. 1 is a schematic of the invention used with a television receiver.

FIG. 1 shows a general embodiment of the invention that includes an interface module 100 and a control module 110. Those skilled in the art will understand that the following describes the functional assembly and operation of the system. Individual components further described herein may be implemented in a number of ways including the use of discrete components, such as capacitors, inductors, resistors, transistors, or by use of integrated circuits. Additionally, the invention may be implemented by use of analog or digital signal processing techniques. Such implementations are deemed included in the invention as well as others that are equivalent to those described herein.

Those skilled in the art will also understand that the invention may be designed into new audio and television equipment, may be incorporated into existing equipment, or may be added to existing equipment as a peripheral improvement. In most audio amplifiers a preamplifier raises the audio signal to a processing threshold level. After the audio signal is processed, filtered or shaped, it is then fed into a power amplifier. The invention provides a control module 110 that, in new equipment, would typically be inserted between the preamplifier and the power amplifier. The control module provides for the independent processing of the preamplifier output signal by audio frequency band.

FIG. 1 shows a typical audio apparatus such as a television 121 that receives input signals via a cable input 124 or an antenna 126. The television includes an audio preamplifier 125 that conditions the detected audio signal from inputs 124 and 126 and an audio power amplifier 127. The output of the power amplifier is applied to the speaker 122. The speaker 122 may be any suitable electro-acoustic transducer including and not limited to one or more loudspeakers for stereophonic reproduction, a headset 122.1 for private listening or a single earphone 122.2. Those skilled in the art will appreciate that while the above example is given in connection with a television, any audio reproduction apparatus may be substituted for a television including a radio, telephone, telephone answering machine, hearing aid, tape deck, compact disk player, MP3 player, remote listening device such as available in concert halls, etc.

The user interface module 100 has a number of control buttons. The test/setup—operating mode button 106 signals the control module 110 to place it into either the test/setup or the operating mode. The remaining interface control module 100 buttons and display are operable when the test/setup mode has been selected. Band select buttons 101 and 102 are pressed to select the individual band of frequencies that are being tested by the invention. The selected frequency band is shown in display box 108. Amplitude buttons 104 and 105 are pressed to, respectively, raise or lower the amplitude of the test tone representative of the frequency band shown in window 108. When button 107 is pressed, control module 110 tests for a minimum threshold level of amplification for frequencies in the selected band of frequencies. When button 109 is pressed, control module 1100 tests for a maximum amplitude level for frequencies in the selected band of frequencies.

Control module 110 typically includes six operating functional elements: a tone generator 116 that generates a sample tone from each frequency band; a group of frequency filters 117 that divide the audio spectrum into a number of bands; a group of adjustable amplifiers 118 that control the signal gain in each frequency band; a group of signal limiters or compressors 119 that control the maximum signal level in each frequency band; circuitry 120 for combining the individual frequency band signals into a single audio signal; a memory 121 for remembering the amplification gain and signal limit of each frequency band established for a particular user through performance of a test/setup procedure, and; means for applying these settings to the amplification and limiting or compression circuitry.

FIG. 1 shows three embodiments for connecting the control module 110 to an audio apparatus in order to apply the invention. The control module 110 may receive a signal from a television audio output jack 123 that carries a reduced voltage version of the audio output signal. Such audio output jacks are found on a number of television models for connecting the audio output of the television to a separate, sound reproduction system. The signal from the audio output jack is connected to the signal input of the control module 110. The control module 110 may have its own power amplifier, use an auxiliary amplifier to power a separate speaker 222, or connect directly to a headphone 122.1 or earphone 122.2. This embodiment would be suitable to add the invention to existing televisions as a peripheral improvement.

A second embodiment of the invention shows the control module 110 connected between the preamplifier 125 and the power amplifier 127 of the television. That embodiment shows the functional relationship for a new television which incorporates the invention. Although the control module is shown outside the perimeter of the television set, those skilled in the art understand that the control module is physically as well as electrically incorporated into the television. Control module 110 receives the output of the preamplifier 125, adjusts the amplitude of frequency bands as determined by the user, and applies the adjusted audio signal to the power amplifier 127 which drives the speaker 122.

Figure 3:
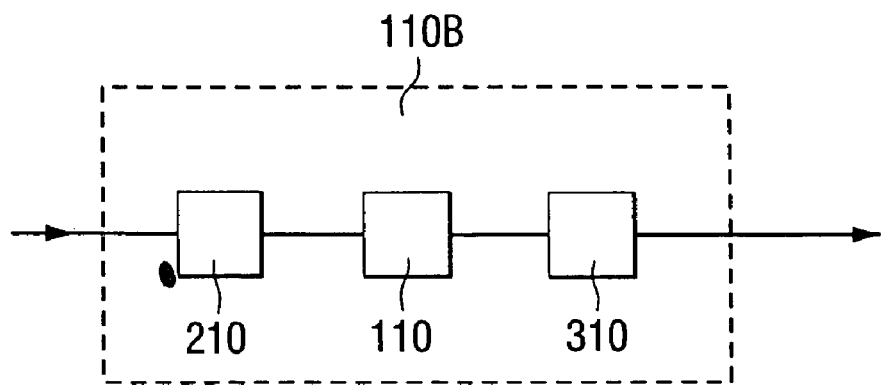
FIG. 3 shows a partial schematic representation of an after market embodiment

In a third embodiment, the control module 110B may be inserted between the output of the power amplifier 127 and the speaker 122. This embodiment could be used for after-market versions of the invention that are operated with existing televisions. Details of the after-market control module 110B are shown in FIG. 3. It includes a transformer 210 that couples the power output signal from the television 121 to the control module 110. Transformer module 210 generates a low voltage audio frequency signal that is proportional to the power output audio signal. The low voltage signal is processed by the control module 110 and its output is applied to a headphone, earphone, or to power amplifier 310 to drive the original television speaker 122 or an auxiliary speaker system 222.

Figure 2:
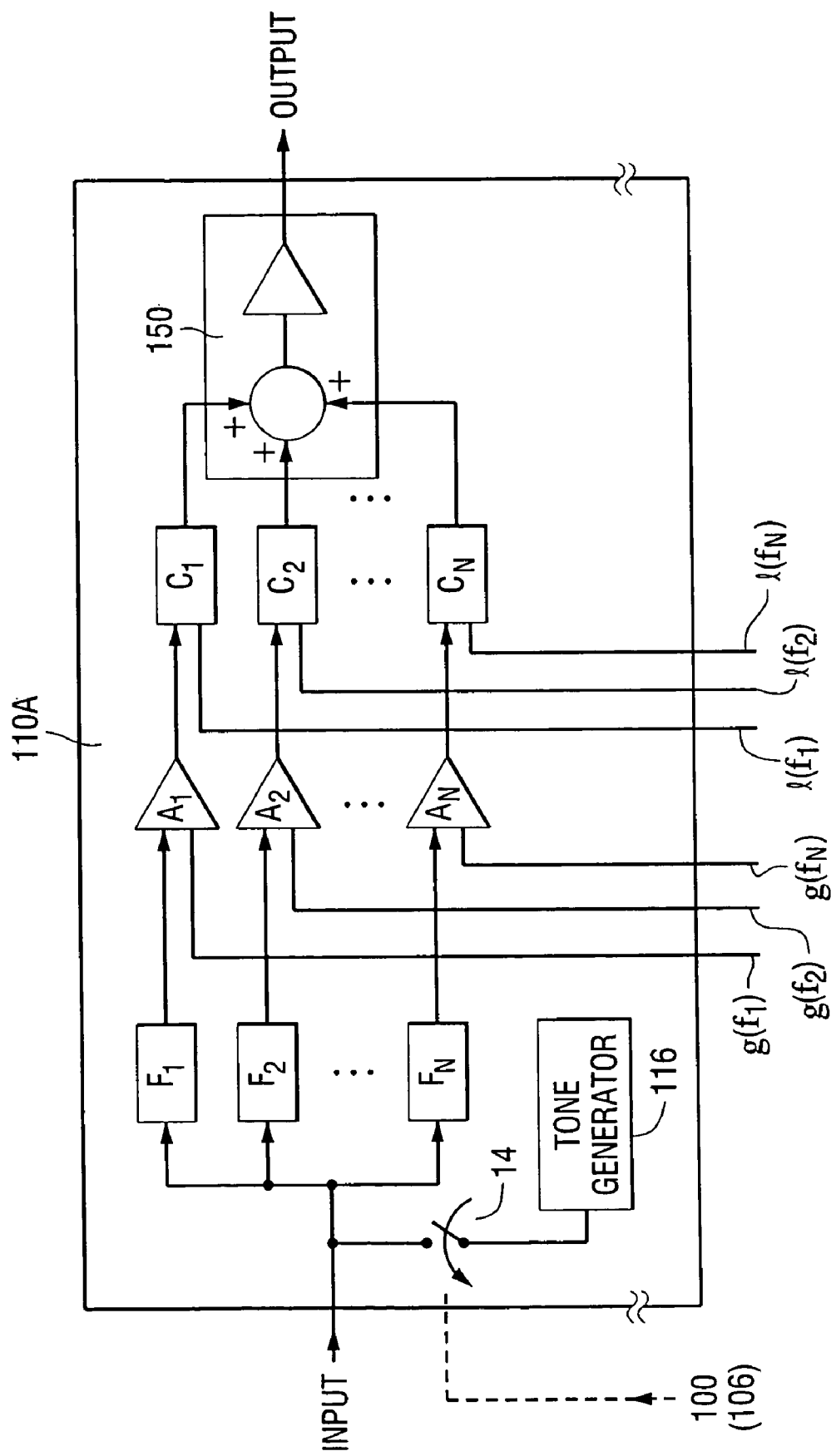
FIG. 2 shows a partial schematic representation of an analog embodiment

The control module 110 may be implemented with either analog or digital signal processing techniques. An analog embodiment is shown in FIG. 2. A representative control module 110A has a plurality of band pass filters $F_1, F_2 \ldots F_N$. In the test/setup mode, a tone generator 116 provides a common input signal to all filters. A switch 14 under control of button 106 on the interface 100 selectively connects the tone generator 116 to the filters $F_1$ to $F_N$. The tone generator 116 generates sample tones in each of the frequency bands that are filtered by the filters $F_1$ to $F_N$. In the operating mode, the audio output jack 123, the preamplifier 125 or the power amplifier 127, coupled through transformer 210, provide a common input to all filters. Each filter passes a band of frequencies different from the other filters. The output of each filter is connected to a corresponding adjustable amplifier $A_1, A_2 \ldots A_N$ whose respective gains are controlled by $g(f_1), g(f_2) \ldots g(f_N)$. The output of each amplifier is connected to a corresponding adjustable limiter or compressor circuit $C_1, C_2 \ldots C_N$ whose maximum outputs are controlled by $l(f_1), l(f_2) \ldots l(f_N)$, respectively. The outputs of all limiter or compressor circuits are combined at the input of the summing amplifier 150 which amplifies all frequency bands equally. The summing amplifier output is applied to the power amplifier input 127, or as otherwise described above.

The above descriptions are meant to be functional examples of the invention. Those skilled in the art understand that there are numerous practical circuits and configurations of analog and digital signal processing elements that can be utilized by those skilled in the art to achieve the signal manipulations of the invention. For example, individual audio compressor and limiter circuits are shown in U.S. Pat. Nos. 3,986,049 and 6,028,944. Still other patents show methods for compressing frequency filtered signals and for using digital signal processors to frequency filter and compress audio signals. See for example U.S. Pat. Nos. 4,233,665; 5,434,923; 5,500,902; 5,781,848, and; 6,104,822 whose entire disclosures are hereby incorporated by reference.

The user interface 100 contains all controls required by an individual to self-administer the test/setup procedure, and thereby to generate their unique hearing adjustment profile The test/setup—operating mode button 106 signals the control module 110 placing it in either the test/setup or operating mode. When the test/setup mode is selected, the tone generator 116 produces a tone at a specific test frequency within the selected frequency band. In one embodiment there are seven bands with frequency ranges in cycles per second and center frequency (CF) for the band as follows:

| | Band | | | | | | |
|---|---|---|---|---|---|---|---|
| | B1 | B2 | B3 | B4 | B5 | B6 | B7 |
| Range | <200 | 200–375 | 375–750 | 750–1.5K | 1.5K–3K | 3K–6K | 6K–20K |
| CF | 125 | 250 | 500 | 1000 | 2000 | 4000 | 8000 |

Each time pressed, button 102 increases the selected frequency band by one band, and button 101 decreases the selected frequency band by one band. Display 108 shows the frequency band selected. The center frequency of the band is often used as the test frequency, but other frequencies could be used. The user may raise or lower the amplitude of the audio output by using buttons 104 or 105, respectively. The increase button 104 raises the level of amplification in steps each time it is pressed. Likewise, the decrease button 105 lowers the amplification in steps each time it is pressed. When a user selects a new frequency band by pressing button 101 or 102, the last amplitude setting for the previous frequency band is captured and held by the control module 110. If button 107 was initially depressed, then the minimum threshold test is being run and the last amplitude setting captured is used to set the amplifier gain g for the previous frequency band. In the example shown in FIG. 2, it is important that no limiting or compression be applied to the audio signal when performing the minimum threshold test. If button 109 was initially depressed, then the last amplitude setting captured is used to set the limiter or compressor maximum signal level l for the previous frequency band.

The user interface 100 is coupled to the control module 110 by signal wires, by infrared or other wireless technique. In the embodiment shown in FIG. 1, the user interface 100 and control module 110 are shown as separate, dedicated components that are used to practice the invention. However, those skilled in the art understand that the functions performed by the dedicated components may be incorporated into conventional remote controls and into the television set.

Figure 4:
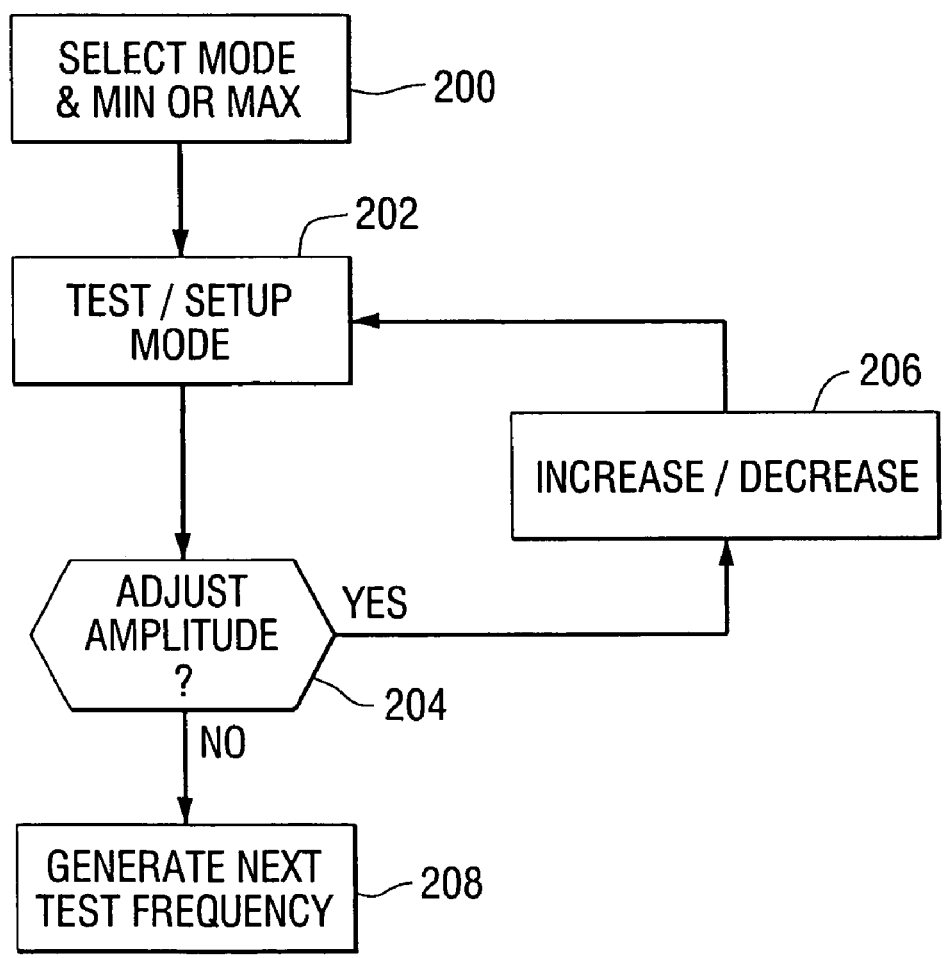
FIG. 4 is a series of steps for performing the invention.

A process for setting the relative amplification of the frequency bands is shown in FIG. 4. The process may be implemented with hardware or software. In use, at step 200 the user selects either the test/setup or operating mode with button 106 and the minimum or maximum sound level test with buttons 107 or 109, respectively. In step 202, the test/setup mode, a test frequency tone is produced in the lowest frequency band. In step 204, the user decides if the sound level requires adjustment. If yes, in step 206 the user increases the test sound level by pushing button 104 one or more times or decreases the amplitude by pushing button 105 one or more times. After the sound is set to the desired level for the first frequency, the user presses the frequency increase button 102 and, in step 208, the next test frequency is generated. If performing a minimum threshold test, then the amplification gain g set when button 102 is pushed is remembered and applied to the amplifier associated with the previous test frequency band. If performing a maximum limit test, then the signal level l at the limiter or compressor output is remembered and applied to the limiting or compressing circuit associated with the previous test frequency band. Each press of button 102 raises the test frequency by one band. The decrease button 101 is used to return to the previous band for retest and reset. When all the bands are set, the user may switch to the operating mode by depressing the test/setup—operating mode button 106 which will also cause the last amplification g(f) or maximum signal level l(f) to be remembered and applied appropriately to control the previous test frequency band circuitry.

With the exception of user acceptance of the appropriateness of the test sound level, and selection of the test/setup mode, all of the process steps described above, including selecting the minimum threshold or maximum level test, changing the test frequency band, increasing or decreasing the test sound level, and recording and applying the accepted gain and level values can be performed automatically, under hardware or software control. Such an automated test/setup procedure is especially useful for example, in programming an automobile audio system where, for safety reasons, driver interaction should be minimized. The following is one example of such an automated procedure. When turned on, the audio system could always start in the operating mode. Pushing button 106 would initiate a preset test/setup procedure. If testing for both minimum threshold and maximum comfort levels, the control module would begin playing the test frequency tone for the first band at a first level of amplification. It would play the tone for one or two seconds before playing the tone again at a higher level. When the user hears the tone, pressing the test/setup button would automatically record the current amplification level and then continue to increase the test tone level until the user indicated that it had reached a maximum comfort level by again pushing the test/setup button 106. When pushed this second time, the test signal is advanced to the next frequency band, and played at one or more levels until the listener again presses the test/setup button twice, acknowledging the levels of amplification. The automatic program changes the frequency band selected until all bands have been tested. Alternatively, the program could test for only minimum threshold or maximum comfort levels. It could also be designed to randomly select test frequencies and sound levels.

The invention may be applied generally to customize the audio output of any audio device to compensate for many types of frequency-related hearing impairments. One of the most common hearing impairments is loss of perception based on frequency. In general, as people grow older, their hearing falls off at higher frequencies. A common frequency-related impairment is a loss in one or more frequency bands. For example, an individual may experience diminished hearing at frequencies of 1–3 kHz and 10–12 kHz relative to their hearing at other frequencies, such as at 60–800 Hz. In order to provide uniform hearing perception, the system may selectively amplify the 1–3 and 10–12 KHz frequencies relative to the 60–800 Hz frequencies. Another common frequency-related hearing impairment affecting perception is an increased sensitivity to high sound levels in various frequency bands. In order to reduce the discomfort of this impairment, the system may limit the maximum sound produced in various frequency bands to different levels.

Figure 5:
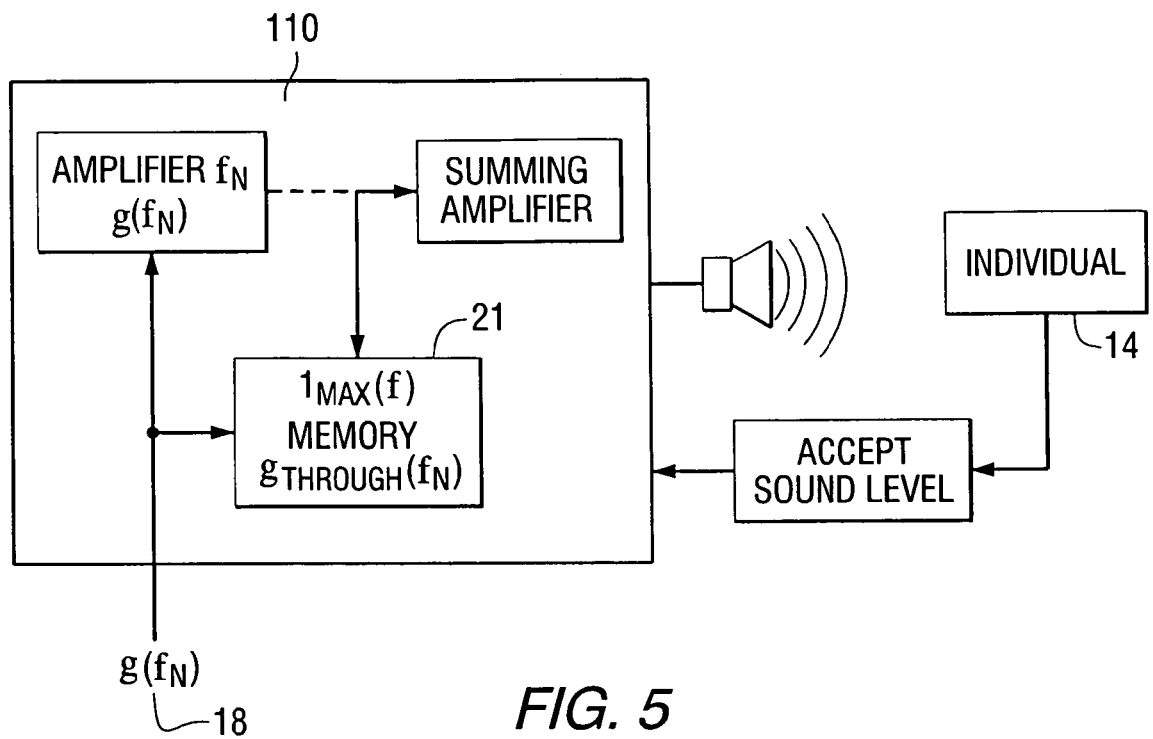
FIG. 5 is a functional diagram showing the invention in the test/setup mode wherein a particular user's hearing adjustment profile is established.
Figure 6:
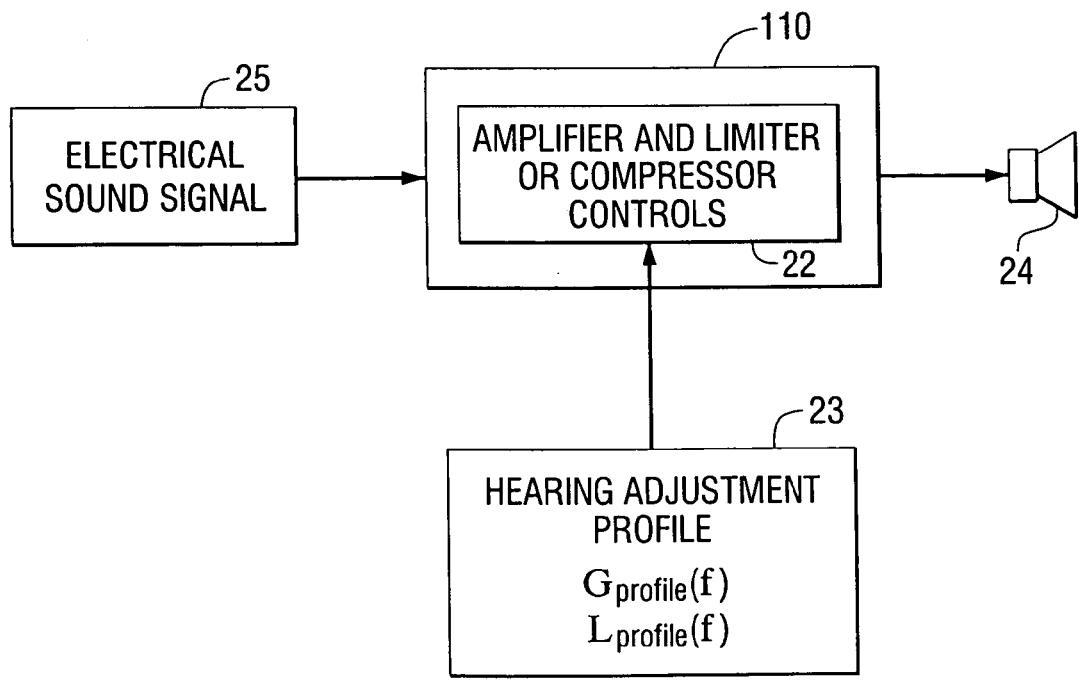
FIG. 6 is a functional diagram showing the invention in the operating mode, wherein the audio output is compensated for a particular user's hearing adjustment profile.

The invention provides a method to compensate for the above types of hearing variations by producing a hearing adjustment profile $G_{profile}$ (f), $L_{profile}$ (f) (23 in FIG. 6) for a given user, as shown generically in FIG. 5. As shown generically in FIG. 6, after the system has established a user's hearing adjustment profile based on the amplitude settings for each frequency band, the audio level in each band from the television, radio or other electrical sound source 25 is shaped by amplifiers, limiters or compressors 22 in accordance with the recorded profile to raise the amplitude of frequencies that are difficult for the user to hear and limit the amplitude of strongly heard frequencies so that the user hears an accurate and comfortable reproduction of the original sound signal from acoustic sound source 24.

The test/setup process, shown generically in FIG. 5, requires varying the amplification gain $g(f_{1,2\ldots N})$ 18 at each test frequency, and recording in the control module memory 21 the gain level, $g_{thresh}(f_{1,2\ldots N})$, at which the individual 14 judges the test frequency sound to be at a minimum audible threshold. Then, the gain is increased until the individual 14 judges the test frequency sound to be at a maximum comfort level and the signal level, $l_{max}(f_{1,2\ldots N})$ at that point is recorded in the control module memory 21. The specific individual's hearing adjustment profile, $G_{profile}$ (f), $L_{profile}$ (f), is the $g_{thresh}(f_{1,2\ldots N})$ and $l_{max}(f_{1,2\ldots N})$ values recorded at all test frequencies. Examples of gain and maximum level values, before and after generating a hearing adjustment profile, are shown in Tables 1 and 2, respectively.

TABLE 1

Initial gain and maximum level settings at each test frequency

| Test Frequency (Hz), f | Gain, g(f) | Maximum level, l(f) |
|---|---|---|
| 125 | 1 | 5 |
| 250 | 1 | 5 |
| ... | 1 ... 1 ... 1 | 5 ... 5 ... 5 |
| 4000 | 1 | 5 |
| 8000 | 1 | 5 |

TABLE 2

Final gain and maximum level settings at each test frequency

| Test Frequency (Hz), f | Gain, $g_{thresh}$(f) | Maximum level, $l_{max}$(f) |
|---|---|---|
| 125 | 4 | 1 |
| 250 | 1 | 2 |
| ... | 2 ... 2 ... 1 | 4 ... 5 ... 3 |
| 4000 | 3 | 2 |
| 8000 | 5 | 5 |

At the end of the test/setup procedure, the listener has created their hearing adjustment profile appropriate for the listening environment in which it was generated. It is stored as $G_{profile}$ (f), $L_{profile}$ (f) values for subsequent control of the audio apparatus.

Those skilled in the art will recognize that some initial $l(f_{1,2\ldots N})$ settings may interfere with producing a useful result. Problems can be avoided if no limiting or compression is applied while assessing $g_{thresh}(f_{1,2...N})$ and $l_{max}(f_{1,2...N})$ values as indicated in Table 1.

A first embodiment of the invention involves adding it to an existing radio, television, or other audio system by attaching the control module 110 input to an appropriate electrical sound signal source within the system, for example the audio output jack or the electrical pre-amplified audio signal, and attaching the control module output to the system's audio power amplifier or to an alternate sound generating circuit.

A second embodiment of the invention includes incorporating the functionality of the first embodiment into new audio equipment. Rather than being physically separate from the audio system and the listening apparatus, the control and interface modules would be internal components of the audio system.

A third embodiment of the invention involves modifying the first or second embodiment to include a microphone so that the audio system can present the subject with locally generated sounds which have been customized by the hearing adjustment profile, in addition to customized sounds from the system's original audio source.

A fourth embodiment of the invention incorporates the functionality of the first embodiment into a hearing aid.

A fifth embodiment of the invention modifies embodiments 1 through 4 to only test for a subject individual's minimum threshold in each frequency band.

A sixth embodiment of the invention modifies embodiments 1 through 5 to automate the test/setup procedure, requiring the user to merely initiate the test/setup process and acknowledge when the test signal is at an acceptable sound level.

The invention claimed is:

1. A method for adjusting the audio output of an apparatus in accordance with a desired level of a listener comprising:
    playing sample tones on the apparatus to generate a hearing adjustment profile of a listener in an uncontrolled audio environment
    generating a hearing adjustment profile by playing at least one sample tone for each one of a number of bands of frequencies and adjusting the level of amplitude of the sample tones until the level of each band reaches an audibility threshold of hearing for the listener for said sample tones;
    adjusting the level of amplitude of each sample tone so that it does not exceed a maximum level of amplitude set by the listener;
    saving the hearing adjustment profile; and
    applying the hearing adjustment profile to the audio apparatus to adjust the audio output of the audio apparatus in accordance with the hearing adjustment profile of the listener.

2. The method of claim 1 wherein the hearing adjustment profile comprises an audio spectrum divided into a plurality of bands of audio frequencies with a user selected level of amplitude for each frequency band.

3. The method of claim 1 wherein the step of applying the hearing adjustment profile comprises adjusting the audio output of the apparatus in accordance with a previously stored hearing adjustment profile.

4. An apparatus providing an audio output adjustable in accordance with a hearing adjustment profile of a listener comprising:
    means for receiving broadcast or prerecorded analog or digital electrical signals representative of audio information;
    means for converting the received or prerecorded analog or digital electrical signals into output audio signals perceptible to a plurality of listeners;
    a tone generator for playing sample tones on the apparatus to generate a hearing adjustment profile of one listener in an uncontrolled audio environment;
    a memory for saving the hearing adjustment profile; and
    a controller for reading the memory and applying the hearing adjustment profile to the apparatus to adjust audio output of the audio apparatus in accordance with the hearing adjustment profile of the one listener and for generating at least one sample tone for each one of a number of bands of frequencies and adjusting the level of amplification of the sample tones until their level reaches an audibility threshold of hearing for the one listener.

5. The apparatus of claim 4 wherein the hearing adjustment profile comprises an audio spectrum divided into a plurality of bands of audio frequencies with a user selected level of amplitude for each frequency band.

6. The apparatus of claim 4 wherein the controller comprises a digital signal processor with a memory for saving the hearing adjustment profile and programs for processing an audio signal to produce an audio output customized in accordance with the hearing adjustment profile of the one listener.

7. The apparatus of claim 4 wherein the controller comprises analog circuitry for processing an audio signal to produce an audio output customized in accordance with the hearing adjustment profile of the one listener.

8. The apparatus of claim 4 wherein the controller further limits or compresses the maximum audio output of each sample tone so that it does not exceed a maximum amplitude set by the one listener.

9. A method for adjusting the audio output of an apparatus in accordance with a desired level of one of a plurality of listeners comprising:
    receiving broadcast or prerecorded analog or digital electrical signals representative of audio information;
    converting the received or prerecorded analog or digital electrical signals into output audio signals perceptible to a plurality of listeners;
    self-administering a hearing test to one listener; and
    applying the results of the self-administered hearing test to the audio apparatus; and
    adjusting the output of the audio apparatus in accordance with the results of the applied hearing test.

10. The method of claim 9 wherein the self-administered hearing test is conducted without a hearing reference.

11. The method of claim 9 wherein the hearing test measures reception of sound at different frequencies.

12. The method of claim 10 wherein the amplitude of each frequency is adjusted until the amplitude is at a minimum audibility level.

13. The method of claim 9 wherein the step of self-administering a hearing test comprises playing sample tones on the apparatus to generate a hearing adjustment profile of said one listener in an uncontrolled audio environment; and
    saving the hearing adjustment profile;
    applying the hearing adjustment profile to the audio apparatus to adjust the audio output of the audio apparatus in accordance with the hearing adjustment profile of said one listener.

14. The method of claim 12 wherein the hearing adjustment profile comprises an audio spectrum divided into a plurality of bands of audio frequencies with a user selected level of amplitude for each frequency band.

15. The method of claim 12 wherein the step of applying the hearing adjustment profile comprises adjusting the audio output of the apparatus in accordance with a previously stored hearing adjustment profile.

16. The method of claim 12 wherein the step of generating a hearing adjustment profile comprises generating at least one sample tone within each band of frequencies and adjusting the level of amplitude of the sample tones until the level of each band reaches an audibility threshold of hearing for the listener for said sample tones.

17. The method of claim 16 comprising the further step of adjusting the level of amplitude of each sample tone so that it does not exceed a maximum level of amplitude set by said one listener.

18. A method for adjusting the audio output of an apparatus in accordance with a self-administered hearing test of a listener comprising:
generating electrical signals representative of audio signals at a location remote from the listener;
converting the electrical signals into audio signals that are perceivable by more than one listener:
self-administering a hearing test to the listener by playing sample audio tones with the apparatus to generate a hearing adjustment profile of said listener in an uncontrolled audio environment;
saving the hearing adjustment profile; and
applying the hearing adjustment profile to the audio apparatus to adjust the audio output of the audio apparatus in accordance with the hearing adjustment profile of said listener.

19. The method of claim 18 wherein the conversion of the electrical signals into audio tones occurs at a location remote from said listener.

20. The method of claim 18 wherein the conversion of the electrical signals into audio signal occurs in a headset disposed on said listener.

21. The method of claim 18 further comprising the step of locating the audio apparatus at a location remote from said listener.

22. The method of claim 18 wherein the hearing adjustment profile comprises an audio spectrum divided into a plurality of bands of audio frequencies with a user selected level of amplitude for each frequency band.

23. The method of claim 18 wherein the step of applying the hearing adjustment profile comprises adjusting the audio output of the apparatus in accordance with a previously stored hearing adjustment profile.

24. The method of claim 18 wherein the step of generating a hearing adjustment profile comprises generating at least one sample tone within each band of frequencies and adjusting the level of amplitude of the sample tones until the level of each band reaches an audibility threshold of hearing for said listener.

25. The method of claim 24 comprising the further step of adjusting the level of amplitude of each sample tone so that it does not exceed a maximum level of amplitude set by said listener.

26. A device for adjusting the audio output of an apparatus in accordance with a desired level of one of a plurality of listeners comprising:
means for receiving broadcast or prerecorded analog or digital electrical signals representative of audio information;
means for converting the received or prerecorded analog or digital electrical signals into output audio signals perceptible to a plurality of listeners;
means for self-administering a hearing test to a listener; and
means for applying the results of the self-administered hearing test to the audio apparatus; and
means for adjusting the output of the audio apparatus in accordance with the results of the applied hearing test.

27. The device of claim 26 wherein the self-administered hearing test is conducted without a hearing reference.

28. The device of claim 26 wherein the self-administered hearing test measures reception of sound at different frequencies.

29. The device of claim 28 wherein the amplitude of each frequency is adjusted until the amplitude is at a minimum audibility level.

30. The device of claim 26 wherein the means for self-administering a hearing test comprises means for playing sample tones on the apparatus to generate a hearing adjustment profile of said listener in an uncontrolled audio environment; and
means for saving the hearing adjustment profile of the listener;
means for applying the hearing adjustment profile of the listener to the audio apparatus to adjust the audio output of the audio apparatus in accordance with the hearing adjustment profile of said listener.

31. The device of claim 29 wherein the hearing adjustment profile comprises an audio spectrum divided into a plurality of bands of audio frequencies wherein the listener selects the level of amplitude for each frequency band.

32. The device of claim 29 wherein the means for applying the hearing adjustment profile comprises means for adjusting the audio output of the apparatus in accordance with a previously stored hearing adjustment profile.

33. The device of claim 29 wherein the means for generating a hearing adjustment profile comprises means for generating at least one sample tone within each band of frequencies and means for adjusting the level of amplitude of the sample tones until the level of each band reaches an audibility threshold of hearing of the listener for said sample tones.

34. The device of claim 33 further comprising means for adjusting the level of amplitude of each sample tone so that it does not exceed a maximum level of amplitude set by said one listener.

* * * * *

UNITED STATES PATENT AND TRADEMARK OFFICE
CERTIFICATE OF CORRECTION

PATENT NO. : 7,190,795 B2
APPLICATION NO. : 10/681718
DATED : March 13, 2007
INVENTOR(S) : Henry Simon Page 1 of 1

It is certified that error appears in the above-identified patent and that said Letters Patent is hereby corrected as shown below:

Col. 1, line 57 "manual" should be --normal--;
Col. 1, line 62, "doctored" should be --doctoral--.

Signed and Sealed this

First Day of May, 2007

JON W. DUDAS
*Director of the United States Patent and Trademark Office*